(12) United States Patent
Moussavi et al.

(10) Patent No.: US 9,931,073 B2
(45) Date of Patent: Apr. 3, 2018

(54) SYSTEM AND METHODS OF ACOUSTICAL SCREENING FOR OBSTRUCTIVE SLEEP APNEA DURING WAKEFULNESS

(75) Inventors: Zahra Moussavi, Manitoba (CA); Amanallah Montazeripouragha, Manitoba (CA)

(73) Assignee: University of Manitoba, Winnipeg (CA)

( * ) Notice: Subject to any disclaimer, the term of this patent is extended or adjusted under 35 U.S.C. 154(b) by 689 days.

(21) Appl. No.: 13/699,462

(22) PCT Filed: May 24, 2011

(86) PCT No.: PCT/IB2011/001119
§ 371 (c)(1),
(2), (4) Date: Jan. 9, 2013

(87) PCT Pub. No.: WO2011/154791
PCT Pub. Date: Dec. 15, 2011

(65) Prior Publication Data
US 2013/0253357 A1    Sep. 26, 2013

Related U.S. Application Data

(60) Provisional application No. 61/347,608, filed on May 24, 2010.

(51) Int. Cl.
*A61B 5/08* (2006.01)
*A61B 5/00* (2006.01)
(Continued)

(52) U.S. Cl.
CPC .......... *A61B 5/4818* (2013.01); *A61B 5/0803* (2013.01); *A61B 5/0826* (2013.01);
(Continued)

(58) Field of Classification Search
CPC ..... A61B 5/087; A61B 5/4806; A61B 5/4818; A61B 7/003
See application file for complete search history.

(56) References Cited

U.S. PATENT DOCUMENTS

| | | | | |
|---|---|---|---|---|
| 6,183,423 B1 * | 2/2001 | Gaumond | .............. | A61B 5/085 600/529 |
| 6,379,311 B1 * | 4/2002 | Gaumond | .............. | A61B 5/085 600/529 |

(Continued)

OTHER PUBLICATIONS

Pasterkamp et al. "Posture-dependent change of tracheal sounds at standardized flows in patients with obstructive sleep apnea." Chest. Dec. 1996;110(6):1493-8.*

(Continued)

*Primary Examiner* — Meredith Weare
(74) *Attorney, Agent, or Firm* — Valauskas Corder LLC (57) ABSTRACT

A system and methods using tracheal sound intensity variations to screen patients suspected of obstructive sleep apnea during wakefulness. The system includes a mechanism positioning the patient and a sound input device attached to a recording device to receive breathing sound signals. A signal conditioning component amplifies and filters the breathing sound signals, and an analog to digital component digitizes the signals. A detecting component detects onsets of respiratory phases, and a separating component separates inspiratory sound signals and expiratory sound signals from the breathing sound signals. A segmenting component segments the inspiratory and expiratory phase signals into a short duration of overlapping windows, and a collection characteristic extraction component obtains characteristics from each window. A calculation component performs statistical analysis to reduce the number of significant charac- (Continued)

teristics and classify the patient as OSA or non-OSA and predicts severity of the OSA as one of mild, moderate and severe.

26 Claims, 7 Drawing Sheets (51) Int. Cl.
    A61B 7/00     (2006.01)
    A61B 7/04     (2006.01)
    G06F 19/00    (2018.01)

(52) U.S. Cl.
    CPC .......... A61B 5/6822 (2013.01); A61B 5/7264 (2013.01); A61B 7/003 (2013.01); A61B 7/04 (2013.01); G06F 19/345 (2013.01); A61B 5/6823 (2013.01); A61B 5/6832 (2013.01); A61B 5/70 (2013.01); A61B 2562/0204 (2013.01)

(56) References Cited

U.S. PATENT DOCUMENTS

| | | | |
|---|---|---|---|
| 6,580,944 B1* | 6/2003 | Katz et al. .................. | 600/513 |
| 7,153,264 B2* | 12/2006 | Katz et al. .................. | 600/300 |
| 7,559,903 B2* | 7/2009 | Moussavi et al. ........... | 600/538 |
| 8,333,696 B2* | 12/2012 | Levendowski et al. ...... | 600/300 |
| 8,880,207 B2* | 11/2014 | Abeyratne et al. ............ | 700/94 |
| 2003/0176788 A1* | 9/2003 | Crutchfield et al. .......... | 600/437 |
| 2005/0171432 A1* | 8/2005 | Crutchfield et al. .......... | 600/454 |
| 2006/0107954 A1* | 5/2006 | Katz et al. ............... | 128/204.23 |
| 2008/0146893 A1* | 6/2008 | Levendowski et al. ...... | 600/300 |
| 2008/0243014 A1* | 10/2008 | Moussavi et al. ........... | 600/529 |
| 2008/0243017 A1* | 10/2008 | Moussavi et al. ........... | 600/532 |
| 2011/0288431 A1* | 11/2011 | Alshaer et al. ............... | 600/534 |
| 2012/0004749 A1* | 1/2012 | Abeyratne et al. ............ | 700/94 |

OTHER PUBLICATIONS

Huq et al. "Breath Analysis of Respiratory Flow using Tracheal Sounds." Dec. 15-18, 2007. 2007 IEEE International Symposium on Signal Processing and Information Technology: 414-418.*
Lofaso et al. "Nasal obstruction as a risk factor for sleep apnoea syndrome." Eur Respir J. Oct. 2000;16(4):639-43.*
Montazeri et al. "Acoustical screening for obstructive sleep apnea during wakefulness." Conf Proc IEEE Eng Med Biol Soc. 2010;2010:3662-5.*
Montazeri et al. "Obstructive Sleep Apnea Prediction During Wakefulness." Conf Proc IEEE Eng Med Biol Soc. 2011;2011:773-6.*
Huq et al., "Breath analysis of respiratory flow using tracheal sounds", IEEE International Symposium on Signal Processing and Information Technology (ISSPIT), pp. 414-418, Dec. 2007.
Le Cam et al., "Acoustical resporatory signal analysis and phase detection", IEEE International Conference on Acoustics, Speech and Signal Processing (ICASSP), pp. 3629-3632, Apr. 2008.
Yadollahi et al., "Acoustic obstructive sleep apnea detection", IEEE Engineering in Medicine and Biology (EMBS), pp. 7110-7113, Sep. 2009.

* cited by examiner

SYSTEM AND METHODS OF ACOUSTICAL SCREENING FOR OBSTRUCTIVE SLEEP APNEA DURING WAKEFULNESS

CROSS-REFERENCE TO RELATED APPLICATION

This application claims the benefit of U.S. Provisional Application Ser. No. 61/347,608, filed May 24, 2010.

FIELD OF THE INVENTION

The invention relates generally to medical devices and methods. More particularly, the present invention relates to a system and methods for screening patients for obstructive sleep apnea. The invention utilizes an acoustical system and methods based on tracheal sound intensity variations for apnea detection during wakefulness.

BACKGROUND OF THE INVENTION

Sleep apnea is a sleep disorder characterized by pauses in breathing during sleep. By definition, sleep apnea is the cessation of airflow to the lungs during sleep which lasts for at least 10 seconds, and is associated with more than a 4% drop of the blood's Oxygen Saturation ("SaO$_2$") level. There are three distinct forms of sleep apnea: central; obstructive; and complex. Complex sleep apnea is defined as a combination of central and obstructive sleep apnea. It is estimated that central, obstructive, and complex sleep apnea account for approximately 0.4%, 84% and 15% of the reported cases, respectively. With central sleep apnea, a patient's breathing is interrupted by the lack of respiratory effort. With obstructive sleep apnea, a physical block to airflow interrupts patient breathing. With complex sleep apnea, there is a transition by a patient from central sleep apnea characteristics to obstructive sleep apnea characteristics during breathing.

Obstructive Sleep Apnea ("OSA") is the most common respiratory disorder. OSA may lead to a myriad of problems such as daytime fatigue, poor job performance, and increased risk of accidents. Additionally, OSA may contribute to cardiovascular problems and irritability and patients may not be able to concentrate. OSA is most common in people with high blood pressure, people with a narrowed airway due to tonsils or adenoids, and people who smoke tobacco products. OSA is also known to occur two to three times more often in the elderly, and also more often in males than in females.

Currently, various tests exist to diagnose sleep apnea such as polysomnography ("PSG"). PSG is a preferred diagnostic tool for sleep apnea and includes a comprehensive recording of the biophysiological changes of a patient that occur during sleep. A typical PSG test consists of recording various biological signals including brain signals ("EEG"), heart rhythm signals ("ECG"), muscle activity or skeletal muscle activation signals ("EMG") of chins and legs, nasal airflow signals, electro-oculogram or eye movement signals ("EOG"), and abdominal and thoracic movement signals. A disadvantage of PSG is the time it takes to gather the biological signals and further the time it takes to evaluate those signals. Another disadvantage of PSG is the expense since the test is administered with a full night of patient supervision by a healthcare professional. Additionally, PSG is neither portable nor convenient for patients. Therefore, many different technological attempts have been made to develop alternative, non-invasive, and portable sleep apnea monitoring tools.

Some of these alternative technologies record a reduced number of signals and detect apnea events during sleep. Many of the current technologies record at least four signals including patient airflow, SaO$_2$, respiratory effort, and snore sound by one or more ambient microphones located within range of the patient. In these technologies, patient airflow may be measured by either a face mask or a nasal cannulae connected to a pressure transducer, and cessation of patient air flow is detected as the main diagnostic sign of sleep apnea, particularly OSA. In the case of mouth breathing by a patient, which may occur often during the night, the nasal cannulae will not register airflow. Therefore, the nasal cannulae is not very reliable. On the other hand, using a face mask, which is considered a more reliable device for airflow measurement, may change the breathing pattern of the patient. Additionally, it is difficult for some patients to fall asleep wearing a face mask.

A majority of people (~70%) who underwent a full-night sleep study are not diagnosed as severely apneic. Therefore, there is a need for a non-invasive system and methods to pre-screen patients suspected of sleep apnea. The present invention satisfies this demand.

SUMMARY OF THE INVENTION

The present invention is a system and methods to pre-screen patients for obstructive sleep apnea ("OSA"), while the patients are in a state of wakefulness or awake. The system and methods are non-invasive and provide patient screening results that are comparable in accuracy to tests using full-night PSG. An acoustical analysis is conducted on the tracheal sound signals to extract the characteristics of a patient's breathing. The use of tracheal respiratory sound represents any airway structural changes. Advantageously, patients suspected of having OSA may be screened using a much more simple testing procedure administered while the patient is awake.

Patients with some degree of upper airway congestion are more prone to develop OSA. Patients with OSA commonly have a defective ability to dilate the pharynx during inspiration. There are noticeable differences between the characteristics, such as intensity, complexity and kurtosis, of nose and mouth breathing sounds of patients with OSA in supine and upright positions compared to non-OSA patients or people who simply snore. The classification of patients with OSA is determined by an apnea/hypopnea index ("AHI"): AHI<5 classifies patients as non-OSA, 5<AHI<15 classifies patients as mild, 15<AHI<30 classifies patients as moderate, and AHI>30 classifies patients as severe.

Tracheal breath sound signals may be recorded in both supine and upright positions during nose and mouth breathing maneuvers. Tracheal breath intensity of patients with OSA increases significantly in the supine position. A Power Spectrum Density ("PSD") of the tracheal breath sound signals in each respiratory phase may be calculated and averaged over the breaths of the patient under test. The spectral features are extracted from the PSD of the one or more breathing sound signals, and investigated for the significant differences in patients with OSA and those patients without OSA. Statistical characteristics of the breathing sound signals are calculated, and characteristics of kurtosis, fractal dimension using a Katz algorithm, and a probability distribution function of the energy of the breathing sound signals are determined. Using the most significant characteristics, which may be determined by statistical tests between an OSA group and a non-OSA group, recorded breathing sound signals of patients may be classified as in an OSA group or a non-OSA group. Furthermore, the system and methods may classify the OSA patients into mild and severe groups.

In one embodiment of the invention, a non-invasive system for screening a patient for obstructive sleep apnea ("OSA") includes a patient positioning mechanism configured to position the patient in at least two positions and a sound input device located adjacent the suprasternal notch of the trachea of the patient. A recording device is connected to the sound input device. The recording device is configured to receive one or more breathing sound signals from the patient. The breathing sound signals are amplified and filtered by a signal conditioning component. A detecting component is configured to detect onsets of respiratory phases by identifying inspiratory phase sound signals and an expiratory phase sound signals from all the digitized breathing sound signals. An analog to digital component is configured to digitize the breathing sound signals. A detecting component is configured to detect onsets of respiratory phases by identifying inspiratory phase sound signals and an expiratory phase sound signals from all of the digitized breathing sound signals. The detected breath onset signals are separated by a separating component that separates the inspiratory phase sound signals and the expiratory phase sound signals from the digitized breathing sound signals.

The system also includes a segmenting component configured to segment each of the inspiratory phase sound signals and the expiratory phase sound signals into a short duration of overlapping windows, wherein each window is defined by a specific time period. A collection characteristic extraction component of the system is configured to obtain data characteristics from each window of the digitized breathing sound signals. The system further includes a calculation component configured to perform statistical analysis to reduce the number of significant characteristics classify the patient as one of an OSA or non-OSA patient, and if the patient is classified in the OSA group, then predicting the severity of the OSA as one of mild, moderate and severe.

In another embodiment of the invention, a non-invasive method for screening a patient for obstructive sleep apnea during wakefulness includes the steps of positioning the patient in at least two positions, locating a sound input device adjacent the suprasternal notch of the trachea of the patient, and collecting in memory breathing sound signals as a result of several breathing maneuvers from the patient. The method also includes steps of amplifying the breathing sound signals, filtering the breathing sound signals in a range of 5 Hz to Fs/2 Hz, where Fs is a sampling rate, and digitizing the breathing sound signals at either a 5,120 Hz sampling rate or a 10,240 Hz sampling rate. Further steps are detecting an onset of each respiratory phase by identifying expiratory phase sound signals and inspiratory phase sound signals from the collected breathing sound signals, and separating the breath onset signals into inspiratory phase sound signals and expiratory phase sound signals from the collected breathing sound signals. Additionally, the method has steps of segmenting each of the inspiratory phase sound signals and the expiratory phase sound signals into a succession of short duration windows with a 50% overlap between the successive windows, performing a statistical analysis to classify the patient as with obstructive sleep apnea or without obstructive sleep apnea, and predicting the severity of the OSA as one of mild, moderate and severe.

In an alternative embodiment, the method may further include a step of determining values of a power spectrum ("Pow"), a Katz Fractal Dimension ("FD"), a Kurtosis ("Kurt") and a probability distribution function ("pdf").

The method may also perform steps of calculating average values from the determining step, wherein the average values are denoted as $Ave^{Pow}$, $Ave^{FD}$, $Ave^{Kurt}$, and $Ave^{pdf}$. The method may perform a step of computing variance values, median calculation values, width values, and peak values of the average values, wherein the variance values are denoted as $Var_{pow}^{ave}$, $Var_{FD}^{ave}$, $Var_{Kurt}^{ave}$ and the median calculation values are denoted as $Med_{pow}^{ave}$, $Med_{FD}^{ave}$, $Med_{Kurt}^{ave}$ and the width values are denoted as $W_{pdf}$ and the peak values are denoted as $P_{pdf}$. Additionally, the method may include a step of recording the average values, the variance values, the median calculation values, the width values and the peak values of said calculating step and said computing step.

Other steps include operating an appropriate statistical test to select one or more characteristics having significant differences (with p-value<0.05) between the OSA group and the non-OSA group, executing a Maximum Relevancy Minimum Redundancy ("mRMR") algorithm to reduce the one or more characteristics to a minimum number, and classifying the patient as having OSA or not having OSA, and if the patient is classified as having OSA, then predicting the severity of the OSA by classification of the patient into any one of a mild group, moderate group and severe group.

The present invention and its methodology and advantages will be further understood and appreciated with reference to the detailed description below of presently contemplated embodiments, taken in conjunction with the accompanying drawings.

BRIEF DESCRIPTION OF THE DRAWINGS

The preferred embodiments of the invention will be described in conjunction with the appended drawings provided to illustrate and not to limit the invention, where like designations denote like elements, and in which.

DETAILED DESCRIPTION OF THE PREFERRED EMBODIMENTS

Figure 1:
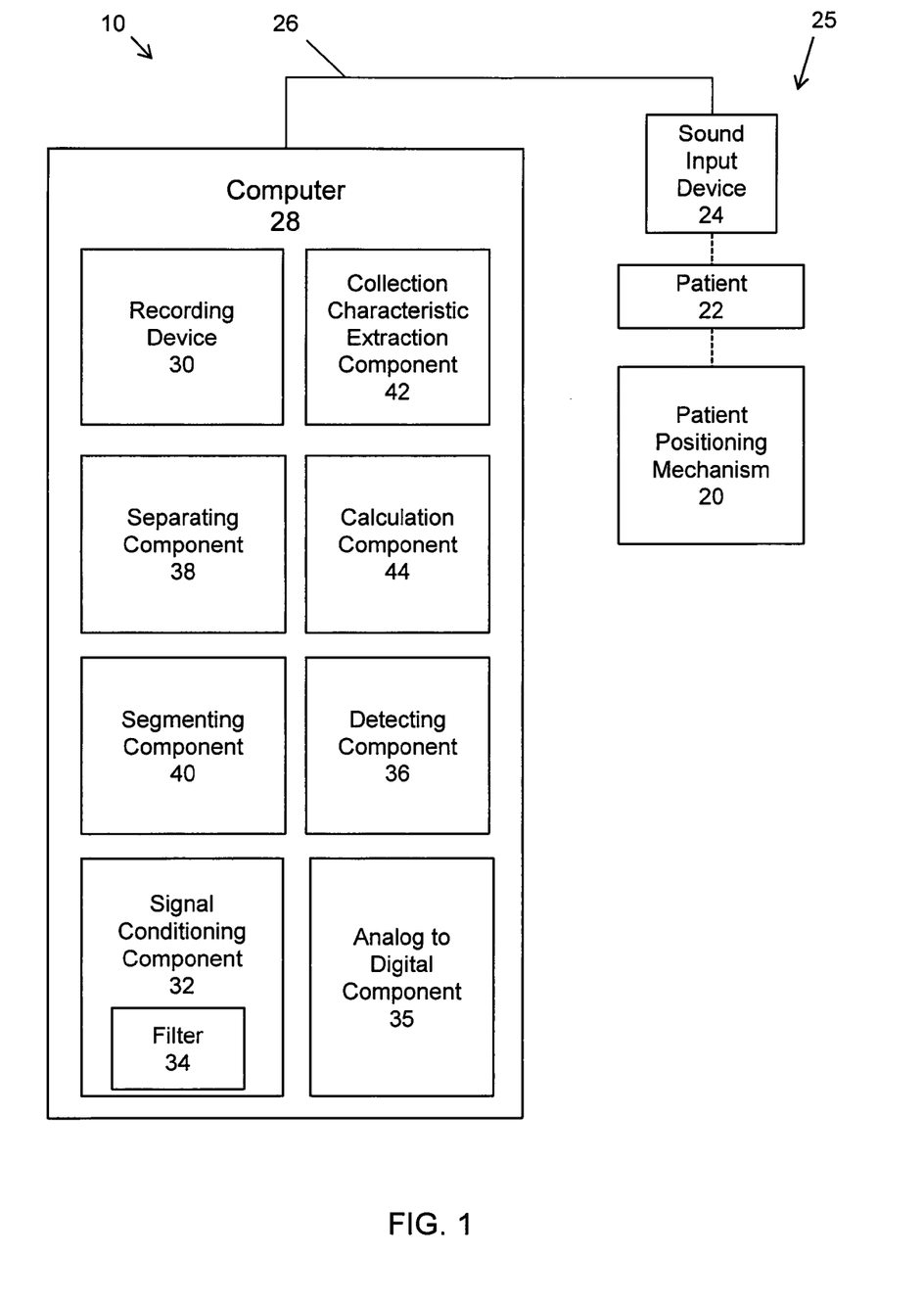
FIG. 1 is a block diagram of a system for screening a patient for obstructive sleep apnea according to one embodiment of the present invention.

FIG. 1 illustrates a system 10 for screening a patient for obstructive sleep apnea according to one embodiment of the present invention. The system 10 includes a patient positioning mechanism 20 for positioning a patient 22 in at least two positions. Preferably, the patient 22 may be positioned in a supine position to collect breathing sound data and an upright position to collect further breathing sound data. However, the number of positions that a patient 22 may be positioned and the breathing sound data collected at each of the patient positions may vary. A user of the system may collect breathing sound data while the patient 22 is in each of these positions.

One advantage of the present system 10 over conventional processes is that the system 10 collects breathing sound data while the patient 22 is in a state of wakefulness. Thus, the present system 10 is more user friendly and accessible than conventional processes which require overnight monitoring of the patient 22 by healthcare professionals.

The system 10 has a sound input device 24 positioned near the patient 22. The sound input device 24 may be any microphone or other device that captures breathing sounds of the patient 22. A user of the system preferably positions the sound input device 24 adjacent the suprasternal notch of the trachea of the patient 22 while the patient 22 is in each of the positions. A group 25 of the patient position mechanism 20, the patient 22, and the sound input device 24 collectively provide an input for further processing by the system 10. A connection line 26 connects the sound input device 24 to a computer 28 having a module 29 and a recording device 30. Module 29 is shown as a single entity, however it is envisioned that the module 29 can be formed of multiple modules. In other embodiments, the sound input device 24 may have a wireless connection to directly connect to the computer 28 and recording device 30.

The recording device 30 is configured to receive the one or more breathing sound signals from the patient 22. The recording device 30 may be, for example, a hard disk drive or other type of storage device of the computer 28. The recording device 30 preferably stores the breathing sound signals for further processing by the computer 28.

The system 10 also includes a signal conditioning component 32 that has a filter 34. The signal conditioning component 32 is configured to modify the one or more breathing sound signals received from the patient 22. Generally, the modification of the breathing sound signals provides an improved digital signal for further processing by the computer 28.

The filter 34 is configured to restrict the breathing sound signals to a range of frequencies or frequency band. In one embodiment, the filter 34 may be a 5-5000 Hz band-pass filter for filtering the one or more breathing sound signals. In an alternative embodiment, the filter 34 may be a 150-1200 Hz Butterworth band-pass filter for filtering the breathing sound signals. An analog to digital component 35 is configured to digitize the breathing sound signals into digital breathing sound signals.

The system further includes a detecting component 36, separating component 38, segmenting component 40, collection characteristic extraction component 42, and calculation component 44. Components 36, 38, 40, 42 and 44 further process the breathing sound signals received by the recording device 30. Each of the components of the module 29 may be implemented in hardware, software, or as a combination of hardware and software. These components of module 29 include elements 32, 34, 35, 36, 38, 40, 42, and 44.

The detecting component 36 operates on the modified signals from the signal conditioning component 32. Using the modified one or more breathing sound signals, the detecting component 36 detects onsets of respiratory phases by identifying inspiratory phase sound signals and an expiratory phase sound signals from all the digitized breathing sound signals. The breath onset signals are then further processed by the separating component 38, which is configured to separate the breath onset signals into inspiratory phase sound signals and expiratory phase sound signals from all the digitized breathing sound signals.

The segmenting component 40 is configured to separate each of the inspiratory phase sound signals and expiratory phase sound signals into a short duration of overlapping windows. Each of the windows that the segmenting component 40 uses has a specific time period. For example, the specific time period for each window may be 20 ms, 50 ms, or some other time period. Moreover, each of the windows may have a percentage overlap with a successive window. By way of example, successive windows may have a 50% overlap.

The collection characteristic extraction component 42 is configured to obtain characteristics from each window of the digitized breathing sound signals. Some data that the collection characteristic extraction component 42 may determine and obtain includes values of a power spectrum ("Pow"), a Katz Fractal Dimension ("FD"), a Kurtosis ("Kurt") and a probability distribution function ("pdf") for each of the segmented inspiratory phase sound signals and the segmented expiratory phase sound signals.

The calculation component 44 is configured to perform statistical analysis to reduce the number of significant characteristics, and classify the patient as one of an OSA patient or non-OSA patient. If the patient is classified in the OSA group, then the calculation component 44 predicts the severity of the OSA as one of mild, moderate and severe. The calculation component may further process the obtained data of the collection characteristic extraction component 42 by calculating average values of the determined values, wherein the average values are denoted as $\text{Ave}^{Pow}$, $\text{Ave}^{FD}$, $\text{Ave}^{Kurt}$, and $\text{Ave}^{pdf}$, and compute variance values, median calculation values, width values, and peak values of the average values. The calculation component calculated variance values are denoted as $\text{Var}_{pow}^{ave}$, $\text{Var}_{FD}^{ave}$, $\text{Var}_{Kurt}^{ave}$, the median calculation values are denoted as $\text{Med}_{pow}^{ave}$, $\text{Med}_{FD}^{ave}$, $\text{Med}_{Kurt}^{ave}$, the width values are denoted as $W_{pdf}$, and the peak values are denoted as $P_{pdf}$.

The calculation component 44 further collects the average values, the variance values, the median calculation values, the width values and the peak values. The calculation component 44 may then perform a statistical test to select one or more characteristics that have significant differences between the OSA group and the non-OSA group, and execute a Maximum Relevancy Minimum Redundancy ("mRMR") algorithm to reduce the selected characteristics to a minimum number, such as two or three characteristics. After executing the mRMR algorithm, the calculation component 44 may classify the patient as one selected from the group of an obstructive sleep apnea patient and a non-apneic patient, and one selected from the group of mild OSA, moderate OSA and severe OSA.

Figure 2:
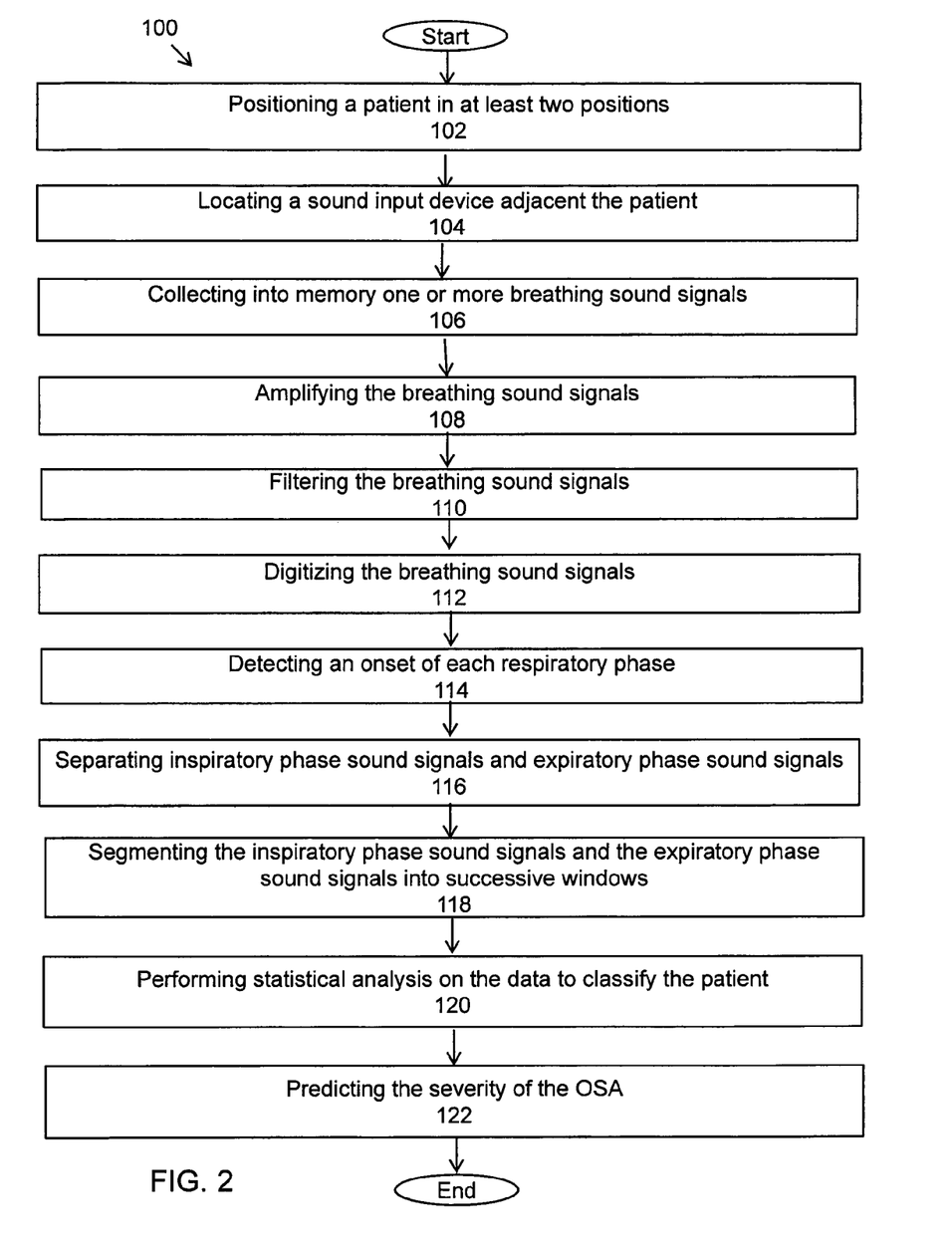
FIG. 2 is a flowchart of a method for screening a patient for obstructive sleep apnea according to one embodiment of the present invention.

Turning now to FIG. 2, a flowchart 100 of a method for screening a patient for obstructive sleep apnea according to one embodiment of the present invention is shown. The method 100 is non-invasive while screening a patient for obstructive sleep apnea during wakefulness. Advantageously, since the method 100 does not need to be performed overnight like many conventional methods, the present method 100 provides a cost savings to health care facilities.

The method 100 starts at Step 102 by positioning the patient in at least two positions, for example the supine position and then the upright position, and locating a sound input device adjacent or near the suprasternal notch of the trachea of the patient at Step 104. The method 100 proceeds at Step 106 to collect into memory breathing sound signals from the patient in at least some of the positions of Step 102. Step 106 collects into memory breathing sound signals as a result of several breathing maneuvers from the patient. The collected breathing sound signals may be obtained from at least one of a nose of the patient and a mouth of the patient. The collected breathing sound signals are amplified at Step 108 and filtered at Step 110. Amplification and filtering may occur by applying different digital signal processing techniques to improve signal quality. Filtering of the breathing sound signals may be in a range of 5 Hz to Fs/2 Hz, where Fs is a sampling rate. For example, a 5-5000 Hz band-pass filter may be used to filter the breathing sound signals. Alternatively, a filtering algorithm including a band-pass filter, such as a 150-1200 Hz Butterworth band-pass filter, may filter the breathing sound signals. The filtering algorithm may be an ANNOVA algorithm. The breathing sound signals may then be digitized at Step 112 at, for example, either a 5,120 Hz sampling rate or a 10,240 Hz sampling rate.

The method 100 detects an onset of each respiratory phase by identifying expiratory phase sound signals and inspiratory phase sound signals from the collected breathing sound signals separated into inspiratory phase sound signals and expiratory phase sound signals at Step 114. Next, the method 100 separates the inspiratory phase sound signals and the expiratory phase sound signals from the collected breathing sound signals at Step 116.

The method 100 takes the inspiratory phase sound signals and expiratory phase sound signals from Step 116 and segments these signals into a succession of short duration windows with a 50% overlap between the successive windows as shown by Step 118. Then, the method 100 performs statistical analysis to classify the patient as one with obstructive sleep apnea or one without obstructive sleep apnea at Step 120. Next, the method proceeds to Step 122 and predicts the severity of the OSA as one of mild, moderate and severe.

Figure 3:
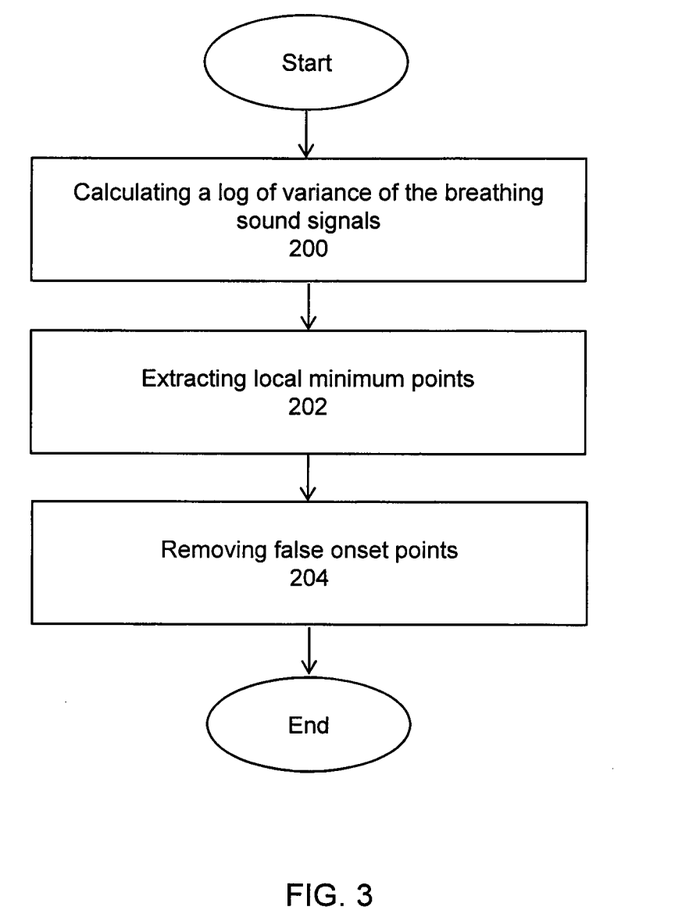
FIG. 3 is a flowchart showing further processing steps of detecting an onset of each respiratory phase of FIG. 2.

FIG. 3 is a flowchart showing additional processing steps of the detecting onset Step 114 of FIG. 2. The method 100 may calculate a log of variance of the breathing sound signals as shown by Step 200. For example, the log of variance of the one or more breathing sound signals may be in 20 ms windows. Then, the method 100 extracts local minimum points 202 of the breathing sound signals as shown by Step 204. The method 100 then removes false onset points at Step 206, and returns to Step 112 of FIG. 1.

Figure 4:
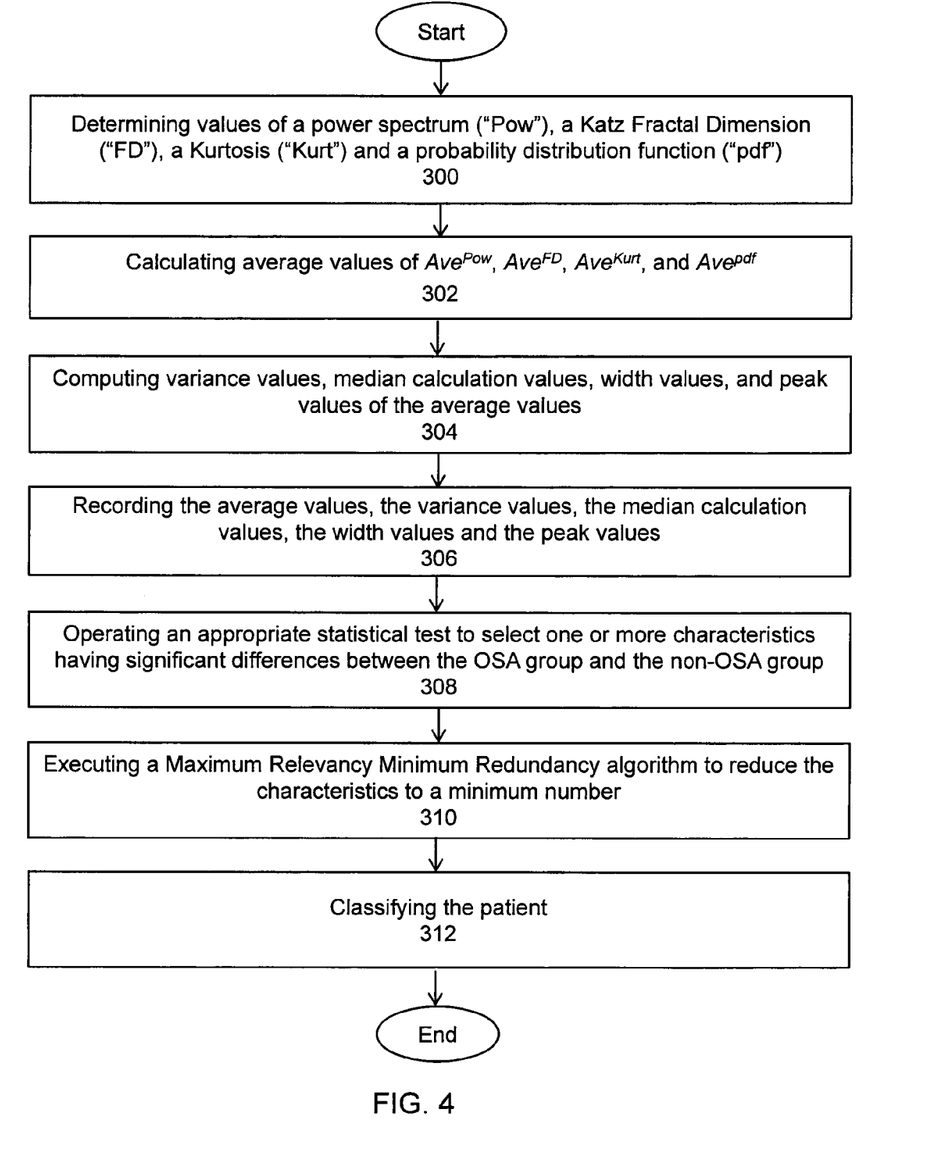
FIG. 4 is a flowchart showing further processing steps of segmenting the inspiratory phase sound signals and the expiratory phase sound signals, and performing a statistical analysis to classify the patient of FIG. 2.

FIG. 4 is a flowchart showing further processing steps of the segmenting at Step 118 and performing statistical analysis at Step 120 of FIG. 2. At Step 118, the method 100 may optionally proceed to Step 300 to determine values of the power spectrum, Katz Fractal Dimension, Kurtosis, and probability distribution function. Then, the method proceeds to Step 302, which begins the performing Step 120 of FIG. 2. The Step 302 calculates the average values of $Ave^{Pow}$, $Ave^{FD}$, $Ave^{Kurt}$, and $Ave^{pdf}$. Next, the variance values, median calculation values, width values, and peak values of the average values are computed (Step 304). The variance values are $Var_{pow}^{ave}$, $Var_{FD}^{ave}$, $Var_{Kurt}^{ave}$ and the median calculation values are $Med_{pow}^{ave}$, $Med_{FD}^{ave}$, $Med_{Kurt}^{ave}$, the width values are $W_{pdf}$, and the peak values are $P_{pdf}$. The average values, variance values, median calculation values, width values and the peak values are then recorded at Step 306.

After the recording Step 306, the method 100 operates an appropriate statistical test to select one or more characteristics having significant differences (with p-value<0.05) between the OSA group and the non-OSA group at Step 308, and executes a Maximum Relevancy Minimum Redundancy algorithm to reduce the one or more characteristics to a minimum number at Step 310. The minimum number may be any integer number, and is preferably two or three. The method 100 next classifies the patient as having OSA or not having OSA, and if the patient is classified as having OSA, then predicting the severity of the OSA by classification of the patient into any one of a mild group, moderate group and severe group at Step 312. The method then ends and returns to Step 120 of FIG. 2. The classification Step 312 may preferably use a quadratic discriminate analysis ("QDA") classification algorithm.

In one exemplary embodiment of the invention, tracheal breathing sound signals are collected by a Sony microphone (ECM-77B) embedded in a chamber (diameter of 6 mm) and placed over the suprasternal notch of a patient's trachea using double-sided adhesive tape. The breathing sound signals are amplified, band pass filtered in a frequency range of 0.05-5000 Hz, and digitized at 10,240 Hz to improve signal quality. The recordings are recorded in two different body positions: upright and supine. In each body position, one or more breathing sound signals are recorded during two breathing maneuvers for at least five full breaths of the patient in each data capture trial. The two breathing maneuvers are breathing through the nose, and then through the mouth with a nose clip in place at a high flow rate, which is the patient's comfortable normal high flow rate.

Inspiration is an active process, while expiration is a passive process. Therefore, the inspiration and expiration phases are analyzed separately. Using a fourth order Butterworth band-pass filter, the recorded breathing sound signals are filtered in the frequency range of 150-1200 Hz to reduce the effects of heart sound and background noise. The onset of each inspiratory phase and expiratory phase are then calculated using, for example, the method 100. The onset detection method is automatically calculated, and optionally the detected onsets may be verified manually for each patient by a healthcare professional to ensure the accuracy. Since the respiratory flow of the patient is not recorded, recording at the inspiration phase is started to ensure proper phase labels.

For each respiratory phase in each breath of the patient, the PSD, fractal dimension and Kurtosis in every 50 ms window with a 50% overlap for successive windows is calculated, and averaged over the segments within the breath phase, which are denoted as $P^{b_i}$, $FD^{b_i}$ and $Kurt^{b_i}$ respectively, where $b_i$ represents the breath number 1 to 5. Next, the average curves of the $P^{b_i}$, $FD^{b_i}$ and $Kurt^{b_i}$ are calculated over five breath cycles for each inspiratory and expiration separately. They are identified as $Ave^{Pow}$, $Ave^{FD}$ and $Ave^{Kurt}$. Then, the variance and median values of these average curves are calculated and denoted as $Var_{pow}^{ave}$, $Med_{pow}^{ave}$, $Var_{FD}^{ave}$, $Med_{FD}^{ave}$, $Var_{Kurt}^{ave}$ and $Med_{Kurt}^{ave}$. These are some of the characteristics. Furthermore, the sounds of each window are normalized by the maximum energy of the breaths of each patient, and a calculation of the probability distribution function of the patient's normalized energy in each of the 50 ms windows occurs. Similar to the procedure for extracting other characteristics, the pdf curves of the five breaths of the patient are averaged for each phase separately to obtain the $Ave^{pdf}$ curve for each patient. Then, the width of $\mu \pm \delta$ as well as the peak of the pdf curve are further characteristics and denoted as $W_{pdf}$ and $P_{pdf}$. These two latter characteristics may show a significant difference between the groups of non-OSA and OSA patients, particularly when comparing the significant differences of these characteristics when the patient is in the two positions of upright and supine.

After recording the patient in two breathing maneuvers and in two different positions, there are four recorded breathing sound signals. Thus, the separation of breathing sound signals in an inspiratory phase and expiratory phase generates eight signals per patient. Optionally, it is possible to investigate the difference between nose and mouth breathing of a patient in each position as well as the differences between the positions in each of the nose and mouth breathing sound signals. In this scenario, extracting the eight characteristics from each breathing sound signal for the above mentioned conditions result in 128 characteristics for consideration with respect to each patient.

In order to obtain statistical data, patients in a test group are divided into two groups: patients with AHI>30 (severe OSA) and with AHI<5 (non-OSA). Then, a one-way ANOVA test was separately performed on each of the characteristics. Twenty-one characteristics were significantly different between the non-OSA and severe OSA groups (p<0.05). These twenty-one characteristics formed a first selected set. Next, the patients of the test group were divided into two groups with AHI>15 and AHI<15. The one-way ANOVA test was separately run again on each of the characteristics. Seventeen characteristics were found to be significantly different between the mentioned groups (p<0.05); these seventeen features formed a second feature set. Then, out of the first and second sets of features, twelve common features were selected for further analysis.

A search algorithm was used to determine the best subspace for classification. The algorithm was a Maximum Relevancy Minimum Redundancy algorithm. The best 2-D subspace was selected for classifying patients with an AHI<15 from those patients with an AHI>15. The Maximum Relevancy Minimum Redundancy algorithm was used to maximize the joint dependency between the characteristics and the target class. This procedure is a Max-Dependency defined as follows:

$$\max D(S,c), D = I(\{x_i, i=1,\ldots,m\};c), \quad \text{Eqn. (1)}$$

where, I represents mutual information; $(\{x_i, i=1,\ldots,m\}; c) = I(S,c)$, and takes the following form:

$$I(S_m, c) = \int \ldots$$
$$\int p(x_1,\ldots,x_m,c) \log \frac{p(x_1,\ldots,x_m,c)}{p(x_1,\ldots,x_m)p(c)} dx_1 \ldots dx_m dc. \quad \text{Eqn. (2)}$$

Since calculating the mutual information using Eqn. (2) is complicated, D(S,c) in Eqn. (1) is approximated with a mean value of all mutual information values between individual features $x_i$ and class c. This procedure a Max-Relevance and defined as follows:

$$\max D(S,c), D = \frac{1}{|s|} \sum_{x_i \in S} I(x_i; c). \quad \text{Eqn. (3)}$$

However, to minimize the dependency between the characteristics, minimal redundancy criterion is defined as follows:

$$\min R(S,c), R = \frac{1}{|s|^2} \sum_{x_i \in s} I(x_i; x_j). \quad \text{Eqn. (4)}$$

By combining Eqn. (3) and Eqn. (4), the minimal-redundancy-maximal-relevance criterion is defined as follows:

$$\max \Phi(D,R), \Phi=D-R. \quad \text{Eqn. (5)}$$

An incremental search method is used to find the subset $S_m$ as follows:

Assume that $S_{m-1}$ is chosen; then, the mth feature will be from the set $\{X-S_{m-1}\}$ by maximizing the following condition:

$$\max_{x_j \in X-S_{m-1}} \left[ I(x_j; c) - \frac{1}{m-1} \sum_{x_i \in S_{m-1}} I(x_i; x_j) \right]. \quad \text{Eqn. (6)}$$

Once the characteristics are selected and reduced, a linear discriminant analysis (LDA) classifier and a quadratic discriminant analysis (QDA) classifier classify patients into different groups. For two group classification the LDA classifier classifies groups by assuming that the conditional probability density functions are both normally distributed with their means calculated from the training set and pooled estimation of the covariance matrix. Under this assumption, the Bayes' optimal solution is to predict points as being from the second class if the ratio of the log-likelihoods is below a prescribed threshold. For the QDA classifier grouping, the classification is the same as the LDA classification grouping except for the estimation of the covariance matrix, which is stratified by the group.

Due to a small number of data in each group, instead of dividing the dataset into a training set and a test set, a Leave-One-Out method is implemented in which every time one patient's data is left out as the test patient while all other patients' data are used as a training set. This procedure is reiterated until all patients' data is used once as a test set. The sensitivity, specificity, and classification accuracy are determined as follows:

Sensitivity: $\frac{TP}{TP+FN}$

Specificity: $\frac{TN}{TN+FP}$

Classification Accuracy: $\frac{\text{Number of correctly classified}}{\text{Number of Total Patients}}$ TP, FN, TN and FP represent the number of correctly classified patients with higher AHI (AHI>30 or AHI>15 in $2^{nd}$ classification), misclassified patients with higher AHI, correctly classified patients with lower AHI (AHI<5 or AHI<15 in $2^{nd}$ classification) and misclassified patients with lower AHI, respectively.

TABLE I

Average age, Body mass index (BMI), AHI values of the patients

| Groups | AGE | BMI | AHI |
|---|---|---|---|
| AHI < 5 | 40.3 ± 8.0 | 26.5 ± 5.7 | 1.3 ± 1.7 |
| AHI > 5 & AHI < 15 | 47.8 ± 9.6 | 30.8 ± 6.3 | 11.4 ± 2.8 |

TABLE I-continued

Average age, Body mass index (BMI), AHI values of the patients

| Groups | AGE | BMI | AHI |
|---|---|---|---|
| AHI > 15 & AHI < 30 | 50.6 ± 6.8 | 29.2 ± 3.1 | 23.8 ± 4.4 |
| AHI > 30 | 49.9 ± 10.4 | 38.4 ± 5.5 | 76.7 ± 40.3 |

The above method has been implemented on 52 patients. Table I above shows demographic information of the patients. The results of Table I show accuracy higher than 90%, with a sensitivity and specificity higher than 92% and 87%, respectively, for predicting severe OSA using QDA classification and only two reduced characteristics.

Figure 5A:
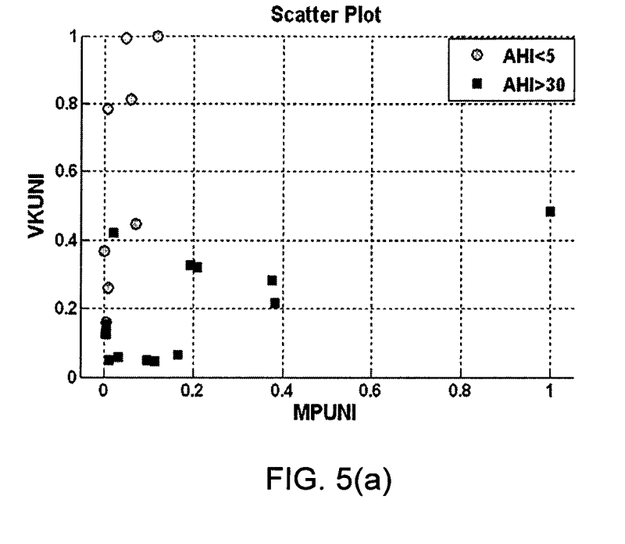
FIGS. 5(a) and 5(b) are graphs showing the scatter plot of two selected characteristics in the classification of different groups with different severity of OSA.
Figure 5B:
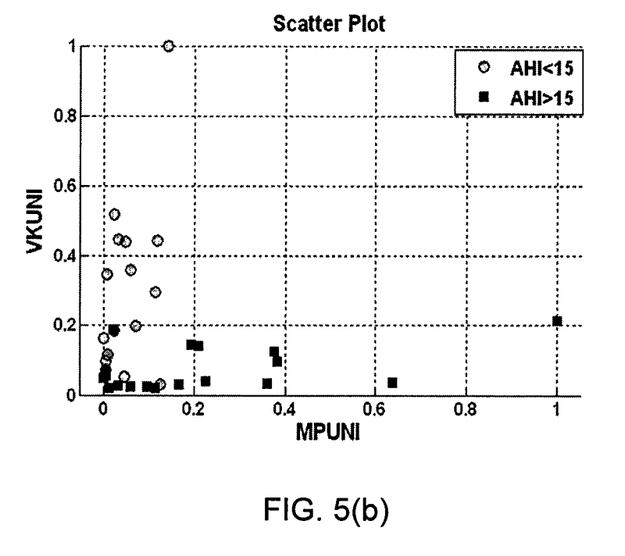
Figure 6:
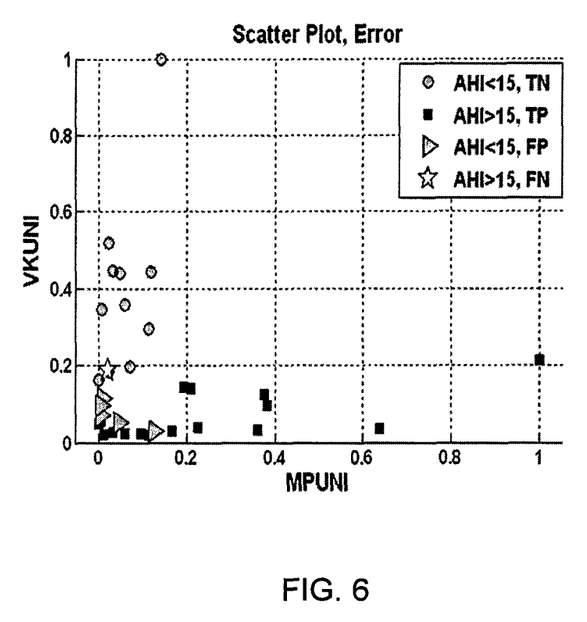
FIG. 6 is a graph showing the classification results using a quadratic discriminate analysis ("QDA") classification.

FIG. 5(a) shows a 2-D scatter plot (MPUNI, VKUNI) for patients with an AHI<5 and an AHI>30. FIG. 5(b) shows a 2-D scatter plot (MPUNI, VKUNI) for patients with an AHI<15 and an AHI>15. FIG. 6 shows a 2-D scatter plot (MPUNI, VKUNI) for patients with an AHI<15 and an AHI>15. The accuracies are based on using a QDA classification. As shown in FIG. 6, there are four different groups; patients with an AHI<15 that are classified correctly (TN); misclassified patients with an AHI<15 (FP); patients with an AHI<5 or an AHI>5 that are classified correctly (TP); and misclassified patients with an AHI>15 (FN).

Figure 7:
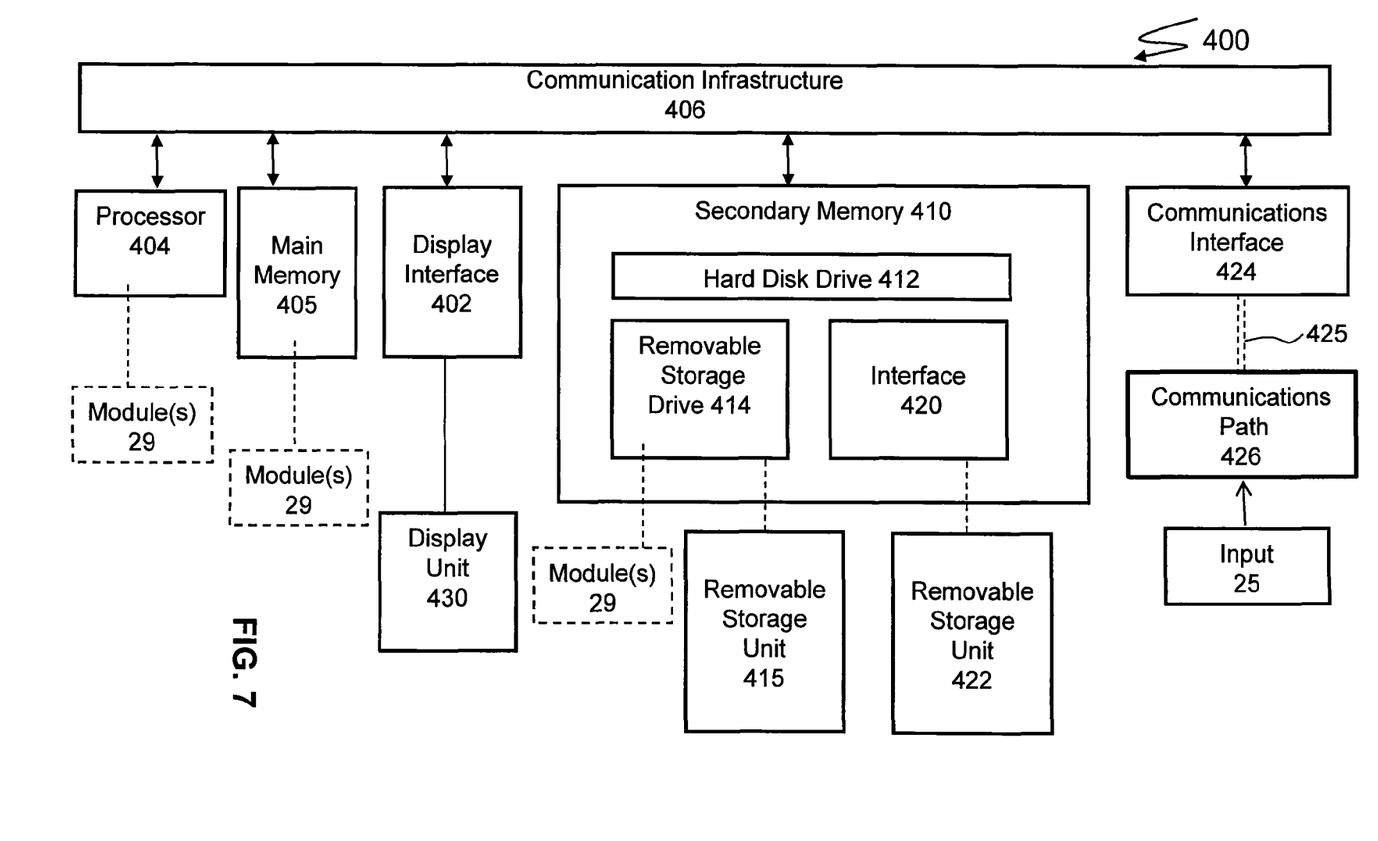
FIG. 7 is a schematic of a computer system for implementing the methods of the invention.

FIG. 7 illustrates an exemplary computer system 400, or network architecture, that may be used to implement the methods according to the present invention. One or more computer systems 400 may carry out the methods presented herein as computer code. One or more processors, such as processor 404, which may be a special purpose or a general-purpose digital signal processor, is connected to a communications infrastructure 406 such as a bus or network. Computer system 400 may further include a display interface 402, also connected to communications infrastructure 406, which forwards information such as graphics, text, and data, from the communication infrastructure 406 or from a frame buffer (not shown) to display unit 430. Computer system 400 also includes a main memory 405, for example random access memory (RAM), read-only memory (ROM), mass storage device, or any combination thereof. Computer system 400 may also include a secondary memory 410 such as a hard disk drive 412, a removable storage drive 414, an interface 420, or any combination thereof. Computer system 400 may also include a communications interface 424, for example, a modem, a network interface (such as an Ethernet card), a communications port, a PCMCIA slot and card, wired or wireless systems, etc.

It is contemplated that the main memory 405, secondary memory 410, communications interface 424, or a combination thereof function as a computer usable storage medium, otherwise referred to as a computer readable storage medium, to store and/or access computer software and/or instructions.

Removable storage drive 414 reads from and/or writes to a removable storage unit 415. Removable storage drive 414 and removable storage unit 415 may indicate, respectively, a floppy disk drive, magnetic tape drive, optical disk drive, and a floppy disk, magnetic tape, optical disk, to name a few.

In alternative embodiments, secondary memory 410 may include other similar means for allowing computer programs or other instructions to be loaded into the computer system 400, for example, an interface 420 and a removable storage unit 422. Removable storage units 422 and interfaces 420 allow software and instructions to be transferred from the removable storage unit 422 to the computer system 400 such as a program cartridge and cartridge interface (such as that found in video game devices), a removable memory chip (such as an EPROM, or PROM) and associated socket, etc.

Communications interface 424 allows software and instructions to be transferred between the computer system 400 and external devices. Software and instructions transferred by the communications interface 424 are typically in the form of signals 425 which may be electronic, electromagnetic, optical or other signals capable of being received by the communications interface 424. Signals 425 are provided to communications interface 424 via a communications path 426. Communications path 426 carries signals 425 and may be implemented using wire or cable, fiber optics, a phone line, a cellular phone link, a Radio Frequency ("RF") link or other communications channels.

Computer programs, also known as computer control logic, are stored in main memory 405 and/or secondary memory 410. Computer programs may also be received via communications interface 424. Computer programs, when executed, enable the computer system 400, particularly the processor 404, to implement the methods according to the present invention. The methods according to the present invention may be implemented using software stored in a computer program product and loaded into the computer system 400 using removable storage drive 414, hard drive 412 or communications interface 424. The software and/or computer system 400 described herein may perform any one of, or any combination of, the steps of any of the methods presented herein. It is also contemplated that the methods according to the present invention may be performed automatically, or may be invoked by some form of manual intervention.

The group 25 of the patient position mechanism 20, patient 22, and sound input device 24 may connect to the system 400 at the communications path 426 and provide input to the system 400. However, it is envisioned that in other embodiments the group 25 may be connected at other parts of the system 400 as is known to those skilled in the art.

The modules 29 are shown in FIG. 7 in dashed lines, and may be connected to different parts of the system 400. By way of example, the modules 29 are shown connected to the processor 404, main memory 405, and secondary memory 410. As is known to those skilled in the art, a single module 29 may be connected to any of these components of the system 400, or alternatively other components of the system 400.

The invention is also directed to computer products, otherwise referred to as computer program products, to provide software to the computer system 400. Computer products store software on any computer useable medium. Such software, when executed, implements the methods according to the present invention. Embodiments of the invention employ any computer useable medium, known now or in the future. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, optical storage devices, Micro-Electro-Mechanical Systems ("MEMS"), nanotechnological storage device, etc.), and communication mediums (e.g., wired and wireless communications networks, local area networks, wide area networks, intranets, etc.). It is to be appreciated that the embodiments described herein may be implemented using software, hardware, firmware, or combinations thereof.

The computer system 400, or network architecture, of FIG. 7 is provided only for purposes of illustration, such that the present invention is not limited to this specific embodiment. It is appreciated that a person skilled in the relevant art knows how to program and implement the invention using any computer system or network architecture.

The described embodiments above are to be considered in all respects only as illustrative and not restrictive, and the scope of the invention is not limited to the foregoing description. Those of skill in the art will recognize changes, substitutions and other modifications that will nonetheless come within the scope of the invention and range of the claims.

It should be understood, however, that there is no intent to limit the disclosure to the particular embodiments disclosed, but on the contrary, the intention is to cover all modifications, equivalents, and alternatives falling within the scope of the disclosure as defined by the appended claims.

What is claimed is:

1. A non-invasive method for screening a patient for classifying obstructive sleep apnea ("OSA") of the patient during wakefulness, comprising the steps of:
    positioning the patient and a training population in each of an upright position and a supine position;
    locating a sound input device adjacent the suprasternal notch of the trachea of the patient and each of the training population;
    collecting by the sound input device trachea breathing sound signals from the patient and from each of the training population in each of the upright position and the supine position to form a collection of breathing sound signals;
    sending the collection of breathing sound signals from the sound input device to a computer system, the computer system comprising a processor and a non-transient computer readable memory, the processor executing a program stored in the memory, the program comprising the steps of:
    storing in the memory the collection of breathing sound signals;
    amplifying by the processor each of the breathing sound signals of the collection;
    filtering by the processor the amplified breathing sound signals in a range of 5 Hz to Fs/2 Hz, where Fs is a first sampling rate;
    digitizing by the processor the filtered breathing sound signals at a second sampling rate, wherein the second sampling rate is either a 5,120 Hz sampling rate or a 10,240 Hz sampling rate;
    detecting by the processor an onset of each respiratory phase by identifying expiratory phase sound signals and inspiratory phase sound signals from the digitized breathing sound signals;
    separating by the processor the inspiratory phase sound signals and the expiratory phase sound signals from the digitized breathing sound signals;
    segmenting by the processor each of the inspiratory phase sound signals and the expiratory phase sound signals into a succession of short duration windows with a 50% overlap between the successive windows;
    determining by the processor values for characteristics of each of the segmented inspiratory phase sound signals and the segmented expiratory phase sound signals from each of the training population and the patient, the characteristics including a power spectrum ("Pow"), a Katz Fractal Dimension ("FD"), a Kurtosis ("Kurt") and a probability distribution function ("pdf");
    defining by the processor the training population to include an OSA group of patients with an Apnea-Hypopnea Index ("AHI")>5 and a non-OSA group of patients with AHI<5, wherein the defining step further comprises selecting the characteristics including the power spectrum ("Pow"), the Katz Fractal Dimension ("FD"), the Kurtosis ("Kurt") and the probability distribution function ("pdf") having a p-value<0.05 identifying significant characteristics showing significant differences between the OSA group and the non-OSA group;
    classifying by the processor the trachea breathing sound signals of the patient according to the significant characteristics showing significant difference between the OSA group and non-OSA group for each of the segmented inspiratory phase sound signals and the segmented expiratory phase sound signals; and
    identifying the patient as an OSA patient or non-OSA patient according to said classification step, and if the patient is classified as an OSA patient, further classifying the patient into any one of a mild group, a moderate group, and a severe group.

2. The non-invasive method for screening a patient for OSA according to claim 1, wherein said detecting step further comprises the steps of:
    calculating by the processor a log of variance (log-var) of all the filtered breathing sound signals;
    extracting by the processor local minimum points of the log-var as onsets of the filtered breathing sound signals of the second filtered set; and
    removing by the processor false onset points by visual inspection and auditory inspection.

3. The non-invasive method for screening a patient for OSA according to claim 2, wherein the log of variance of the filtered breathing sound signals is in 20 ms successive windows.

4. The non-invasive method for screening a patient for OSA according to claim 1, wherein said defining step further comprises the steps of:
    calculating by the processor average values for each of the characteristics from each of the training group and the patient;
    computing by the processor variance values, median calculation values, width values, and peak values of the average values for each of the characteristics from each of the training group and the patient;
    recording to the memory the average values, the variance values, the median calculation values, the width values, and the peak values; and
    reducing by the processor the significant characteristics to a minimum number of significant characteristics for each of the OSA group and non-OSA group using a Maximum Relevancy Minimum Redundancy ("mRMR") algorithm.

5. The non-invasive method for screening a patient for OSA according to claim 4, wherein the minimum number of the significant characteristics is two.

6. The non-invasive method for screening a patient for OSA according to claim 4, wherein said classifying step further comprises the step of applying a quadratic discriminate analysis ("QDA") classification algorithm or a linear discriminant analysis ("LDA") classification algorithm.

7. The non-invasive method for screening a patient for OSA according to claim 1, wherein said collecting step records the breathing sound signals from at least two types of breathing including nose breathing and mouth breathing with a nose clip attached to the patient.

8. The non-invasive method for screening a patient for OSA according to claim 1, wherein said filtering step further comprises the step of using a filtering algorithm including a 150-1200 Hz Butterworth band-pass filter to filter the collected breathing sound signals.

9. The non-invasive method for screening a patient for OSA according to claim 1, wherein said defining step further comprises the step of applying an ANOVA algorithm.

10. The non-invasive method for screening a patient for OSA according to claim 1, wherein the sound input device is a microphone.

11. The non-invasive method for screening a patient for OSA according to claim 1, wherein the short duration is 50 ms.

12. A system for screening a patient for obstructive sleep apnea ("OSA"), comprising:
a processor comprising a signal conditioning component, an analog to digital component, a detecting component, a separating component, a segmenting component, a collection characteristic extraction component and a calculation component;
a program stored on a non-transient computer readable memory;
a patient positioning mechanism positioning the patient and a training population in at least two positions;
a sound input device located adjacent the suprasternal notch of the trachea of the patient and the training population;
a recording device connected to said sound input device, the recording device receiving and recording breathing sound signals from the patient and the training population in each of the two positions;
the processor operatively coupled to the recording device, the processor executing the program to provide the following instructions to each component:
the signal conditioning component amplifying and filtering the breathing sound signals from the patient and the training population in each of the two positions to provide a filtered set;
the analog to digital component digitizing the breathing sound signals of the filtered set to produce a set of digitized breathing sound signals;
the detecting component detecting onsets of respiratory phases by identifying inspiratory phase sound signals and expiratory phase sound signals of the digitized set;
the separating component separating the inspiratory phase sound signals and the expiratory phase sound signals of the digitized set;
the segmenting component segmenting each of the inspiratory phase sound signals and the expiratory phase sound signals of the digitized set into a short duration of overlapping windows, wherein each of the overlapping windows is defined by a specific time period;
the collection characteristic extraction component determining values for characteristics from each of the overlapping windows of the segmented inspiratory phase sound signals and the segmented expiratory phase sound signals of the digitized set, the characteristics comprising of a power spectrum ("Pow"), a Katz Fractal Dimension ("FD"), a Kurtosis ("Kurt"), and a probability distribution function ("pdf") for;
the calculation component performing a statistical analysis on the training population, the training population including an OSA group and a non-OSA group, to select the characteristics including the power spectrum ("Pow"), the Katz Fractal Dimension ("FD"), the Kurtosis ("Kurt") and the probability distribution function ("pdf") having significant differences (p-value<0.05) between the OSA group and the non-OSA group, the OSA group defined by patients with an Apnea-Hypopnea Index ("AHI")>5 and the non-OSA group defined by patients with an AHI<5; and
the calculation component, based on the statistical analysis, classifying the breathing sound signals of the patient according to the selected characteristics having significant differences between the OSA group and the non-OSA group of the inspiratory phase sound signals and the expiratory phase sound signals to identify the patient as one of an OSA or non-OSA patient, and, if the patient is classified as a OSA patient, further classify the patient as one selected from the group of mild OSA, moderate OSA, and severe OSA.

13. The system for screening a patient for OSA according to claim 12, wherein said calculation component further calculates a log of variance of all the recorded breathing sound signals of the digitized set, extracts local minimum points of the log or of variance as onsets of the recorded breathing sound signals of the digitized set, and removes false onset points.

14. The system for screening a patient according to claim 13, wherein said calculation component further:
calculates average values of the determined values for each of the training group and the patient, wherein the average values are denoted as $Ave^{Pow}$, $Ave^{FD}$, $Ave^{Kurt}$, and $Ave^{pdf}$;
computes variance values, median calculation values, width values, and peak values of the average values for each of the training group and the patient, wherein the variance values are denoted as $Var_{pow}^{ave}$, $Var_{FD}^{ave}$, $Var_{Kurt}^{ave}$ and the median calculation values are denoted as $Med_{pow}^{ave}$, $Med_{FD}^{ave}$, $Med_{Kurt}^{ave}$ and the width values are denoted as $W_{pdf}$ and the peak values are denoted as $P_{pdf}$;
collects the average values, the variance values, the median calculation values, the width values, and the peak values; and
executes a Maximum Relevancy Minimum Redundancy ("mRMR") algorithm to reduce a number of selected characteristics to a minimum number.

15. The system for screening a patient for OSA according to claim 12, wherein the signal conditioning component filters the recorded breathing sound signals of the filtered set using a filtering algorithm.

16. The system for screening a patient for OSA according to claim 15, wherein the filtering algorithm includes a 150-1200 Hz Butterworth band-pass filter to filter the breathing sound signals.

17. The system for screening a patient for OSA according to claim 12, wherein the at least two positions comprises a supine position and an upright position.

18. A non-invasive method for screening a patient for obstructive sleep apnea ("OSA") during wakefulness, comprising the steps of:
positioning the patient and a training population in two or more positions;
locating a sound input device adjacent the suprasternal notch of the trachea of the patient and the training population;
collecting by the sound input device breathing sound signals from the patient and the training population as a result of nose breathing and mouth breathing in each of the two or more positions to form a collection of breathing sound signals;

sending the collection of breathing sound signals from the sound input device to a computer system, the computer system comprising a processor and a non-transient computer readable memory, the processor executing a program stored on the memory, the program comprising the steps of:

amplifying each of the breathing sounds signals;

filtering the amplified breathing sound signals in a range of 5 Hz to Fs/2 Hz, where Fs is a first sampling rate, providing a first filtered set;

digitizing the filtered breathing sound signals of the first filtered set at a second sampling rate, wherein the second sampling rate is either a 5,120 Hz sampling rate or a 10,240 Hz sampling rate, providing a second filtered set;

detecting an onset of each respiratory phase by identifying expiratory phase sound signals and inspiratory phase sound signals from the second filtered set;

separating the inspiratory phase sound signals and the expiratory phase sound signals from the second filtered set;

segmenting each of the inspiratory phase sound signals and the expiratory phase sound signals from the second filtered set into a succession of short duration windows with a 50% overlap between the successive windows, determining by the processor values for characteristics of each of the inspiratory phase sound signals and the expiratory phase sound signals from the second filtered set, the characteristics including a power spectrum ("Pow"), a Katz Fractal Dimension ("FD"), a Kurtosis ("Kurt") and a probability distribution function ("pdf");

defining by the processor the training population to include an OSA group and a non-OSA group, and selecting the characteristics including the power spectrum ("Pow"), the Katz Fractal Dimension ("FD"), the Kurtosis ("Kurt") and the probability distribution function ("pdf") having a p-value<0.05 identifying significant differences between the OSA group and the non-OSA group, the OSA group defined by patients with an Apnea-Hypopnea Index ("AHI")>5 and the non-OSA group defined by patients with an AHI<15; and classifying by the processor the collected breathing sound signals of the patient according to the selected characteristics identifying significant differences between the OSA group and non-OSA group of the inspiratory phase sound signals and the expiratory phase sound signals to classify the patient as an OSA patient or non-OSA patient, and if the patient is classified as a OSA patient, further classifying the patient into any one of a mild group, a moderate group, and a severe group.

19. The non-invasive method for screening a patient for OSA according to claim 18, wherein said detecting step further comprises the steps of: calculating a log of variance (log-var) of the inspiratory phase sound signals and the expiratory phase sound signals from the second filtered set;

extracting local minimum points of the log-var as onsets of the inspiratory phase sound signals and the expiratory phase sound signals from the second filtered; and removing false onset points by visual inspection and auditory inspection.

20. The non-invasive method for screening a patient for OSA according to claim 19, wherein said determining step further comprises the steps of:

calculating average values from said determining step of the training population and the patient, wherein the average values are denoted as $Ave^{Pow}$, $Ave^{FD}$, $Ave^{Kurt}$, and $Ave^{pdf}$;

computing variance values, median calculation values, width values, and peak values of the average values of the training population and the patient, wherein the variance values are denoted as $Var_{pow}^{ave}$, $Var_{FD}^{ave}$, $Var_{Kurt}^{ave}$ and the median calculation values are denoted as $Med_{pow}^{ave}$, $Med_{FD}^{ave}$, $Med_{Kurt}^{ave}$ and the width values are denoted as $W_{pdf}$ and the peak values are denoted as $P_{pdf}$;

recording the average values, the variance values, the median calculation values, the width values, and the peak values of said calculating step and said computing step;

reducing by the processor the selected characteristics to a minimum number using a Maximum Relevancy Minimum Redundancy ("mRMR") algorithm.

21. The non-invasive method for screening a patient for OSA according to claim 20, wherein the minimum number of the significant characteristics is two.

22. The non-invasive method for screening a patient for OSA according to claim 20, wherein said classification step further comprises the step of applying a quadratic discriminate analysis ("QDA") classification algorithm or a linear discriminant analysis ("LDA") classification algorithm.

23. The non-invasive method for screening a patient for OSA according to claim 19, wherein the log of variance of the breathing sound signals is in 50 ms windows with a 50% overlap between the successive windows.

24. The non-invasive method for screening a patient for OSA according to claim 18, wherein said filtering step further comprises the step of using a filtering algorithm including a 150-1200 Hz Butterworth band-pass filter to filter the collected breathing sound signals.

25. The non-invasive method for screening a patient for OSA according to claim 18, wherein said identifying step further comprises the step of applying an ANOVA algorithm.

26. The non-invasive method for screening a patient for OSA according to claim 18, wherein the at least two positions comprise a supine position and an upright position.

* * * * *